(12) United States Patent
Boscan et al.

(10) Patent No.: US 9,446,029 B2
(45) Date of Patent: Sep. 20, 2016

(54) USE OF NK-1 RECEPTOR ANTAGONISTS IN MANAGEMENT OF VISCERAL PAIN

(75) Inventors: Pedro Boscan, Bellvue, CO (US); David Twedt, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 452 days.

(21) Appl. No.: 13/192,283

(22) Filed: Jul. 27, 2011

(65) Prior Publication Data

US 2012/0028980 A1 Feb. 2, 2012

Related U.S. Application Data

(60) Provisional application No. 61/368,102, filed on Jul. 27, 2010, provisional application No. 61/478,189, filed on Apr. 22, 2011.

(51) Int. Cl.

| A61K 31/535 | (2006.01) |
|---|---|
| A01N 43/90 | (2006.01) |
| A61K 31/44 | (2006.01) |
| A61K 31/497 | (2006.01) |
| A61K 31/439 | (2006.01) |
| A61K 31/496 | (2006.01) |
| A61K 31/5377 | (2006.01) |

(52) U.S. Cl.
CPC ........... *A61K 31/439* (2013.01); *A61K 31/496* (2013.01); *A61K 31/5377* (2013.01)

(58) Field of Classification Search
CPC ............. A61K 31/439; A61K 31/496; A61K 31/5377
USPC ................. 514/236.2, 305, 253.01
See application file for complete search history.

(56) References Cited

U.S. PATENT DOCUMENTS

| 4,839,465 | A | 6/1989 | Singh et al. | |
|---|---|---|---|---|
| 5,576,317 | A | 11/1996 | Gonsalves | |
| 5,691,336 | A | 11/1997 | Dorn et al. | |
| 5,719,147 | A | 2/1998 | Dorn et al. | |
| 6,096,742 | A | 8/2000 | Crocker et al. | |
| 6,387,925 | B1 | 5/2002 | Quallich et al. | |
| 2005/0256164 | A1 * | 11/2005 | O'Neill et al. | 514/317 |
| 2007/0129328 | A1 * | 6/2007 | Boettner et al. | 514/58 |
| 2007/0155782 | A1 | 7/2007 | Hickman et al. | |
| 2009/0099364 | A1 | 4/2009 | Basford et al. | |
| 2009/0221641 | A1 * | 9/2009 | Janssens et al. | 514/322 |

FOREIGN PATENT DOCUMENTS

| EP | 0284942 A2 | 10/1988 |
|---|---|---|
| EP | 0327009 A1 | 8/1989 |
| EP | 0446706 A2 | 9/1991 |
| EP | 0482539 A2 | 4/1992 |
| EP | 0484719 A2 | 5/1992 |
| GB | 2216529 | 10/1989 |
| WO | 9102745 A1 | 3/1991 |
| WO | 9112266 A1 | 8/1991 |
| WO | 0118016 A1 | 3/2001 |

OTHER PUBLICATIONS

Glerum et al. (Veterinary Surgery, 30, 351-358, 2001).*
Devitt et al. (JAVMA, 227, 6, Sep. 15, 2005).*
Papich (Veterinary Pharmacology and Therapeutics, Ninth Edition, 2009, p. 1247-1272, editors: Jim E. Riviere Mark G. Papich).*
Bradesi et al. (Gastroenterology, 2006, 130, 1729-1742).*
Heard, D.J. et al, Effect of acepromazine on the anesthetic requirement of halothane in the dog, AJVR, 1986, pp. 2113-2115, vol. 47, No. 10.
Hellyer, P.W. et al, Effects of diazepam and flumazenil on minimum alveolar concentrations for dogs anesthetized with isoflurane or a combination of isoflurane and fentanyl, AJVR, 2001, pp. 555-560, vol. 62, No. 4.
Muir, W.W. III, et al, Effects of morphine, lidocaine, ketamine, and morphine-lidocaine-ketamine drug combination on minimum alveolar concentration in dogs anesthetized with isoflurane, AJVR, 2003, pp. 1155-1160, vol. 64, No. 9.
Murphy, M.R. and Hug, C. C. Jr., The Enflurane Sparing Effect of Morphine, Butorphanol, and Nalbuphine, Anesthesiology, 1982, pp. 489-492, vol. 57.
Pascoe, P.J. et al, Changes in the minimum alveolar concentration of isoflurane and some cardiopulmonary measurements during three continuous infusion rates of dexmedetomidine in dogs, Veterinary Anaesthesia and Analgesia, 2006, pp. 97-103, vol. 33.
Pypendop, B.H. et al, Characteristics of the relationship between plasma ketamine concentration and its effect on the minimum alveolar concentration of isoflurane in dogs, Veterinary Anaesthesia and Analgesia, 2007, pp. 209-212, vol. 34.
Steffey, E.P. et al, Influence of Inhaled Anesthetics on the Pharmacokinetics and Pharmacodynamics of Morphine, Anesth Analg, 1993, pp. 346-351, vol. 77.
Valverde, A. et al, Effect of lidocaine on the minimum alveolar concentration of isoflurane in dogs, Veterinary Anaesthesia and Analgesia, 2004, pp. 264-271, vol. 31.
Yamashita, K. et al, Effects of Carprofen and Meloxicam with or without Butorphanol on the Minimum Alveolar Concentration of Sevoflurane in Dogs, J. Vet. Med. Sci., 2008, pp. 29-35, vol. 70, No. 1.
Ishizaki, K., et al., *Intrathecal Neurokinin-1 Receptor Antagonist Reduces Isoflurane MAC in Rats*, 44:5 Can J Anaesth pp. 543-549, (1997).
Stevenson, G.W., et al., *Targeting Pain-Depressed Behaviors in Preclinical Assays of Pain and Analgesia: Drug Effects on Acetic Acid-Depressed Locomotor Activity in ICR Mice*, 85 Life Sci. 309, Abstract (2009).

* cited by examiner

*Primary Examiner* — Uma Ramachandran
(74) *Attorney, Agent, or Firm* — Polsinelli PC

(57) ABSTRACT

Methods for managing visceral pain in mammalian subjects are described, in which a NK-1 receptor antagonist is administered to the subject before, during or after administration of general anesthesia. The methods and uses of NK-1 receptor antagonists described herein provide improved visceral pain management and MAC reduction when used with volatile anesthetics for general anesthesia.

15 Claims, 7 Drawing Sheets

USE OF NK-1 RECEPTOR ANTAGONISTS IN MANAGEMENT OF VISCERAL PAIN

RELATED APPLICATION INFORMATION

This application claims the benefit of U.S. provisional application No. 61/368,102 filed Jul. 27, 2010, and U.S. provisional application No. 61/478,189, filed Apr. 22, 2011, the entire disclosures of which are herein incorporated by reference.

TECHNICAL FIELD

The present disclosure relates generally to methods for managing pain, and in particular to methods for managing visceral pain in mammals.

BACKGROUND OF THE INVENTION

Volatile anesthetics are commonly used to achieve the appropriate plane of anesthesia in human and veterinary surgical patients. Volatile anesthetics are however costly and have certain side effects such as reducing vascular resistance and resulting hypotension. It therefore can be desirable to reduce the amount, typically determined as minimum alveolar concentration or "MAC", of the volatile anesthetic needed during painful procedures through use of a MAC reducing agent. Known MAC reducing agents include opiates such as morphine and fentanyl, ketamine, lidocaine and dexmedetomidine.

Opioid compounds in particular are capable of dramatic MAC reductions of 50% and higher. For example, morphine is currently used as a standard MAC reduction agent in the veterinary field. The use of morphine and other opioids however incurs numerous disadvantages related to the fact that these substances are highly addictive and thus are classified as controlled substances under DEA regulations. Use of these substances requires a license from the DEA to use, and are subject to additional strict control measures including secure storage under lock and key, and detailed logging of when and how each dose is used or disposed. Routine maintenance of opioids in a clinic runs the risk of abuse by anyone with access to the supply including veterinary clinic staff members, and the risk of break-in and theft of the substances by anyone else seeking unlawful use. Additionally, morphine and other opioids commonly used for pain management in veterinary medicine often induce undesirable mental and behavioral changes in certain animals including dogs, including for example lethargy and dysphoria. Other side effects associated with morphine and other opioids in dogs and other species include a decrease in gastrointestinal motility and increase in incidence of complications such as constipation, increase in urinary retention which predisposes to damage of the urinary tract, and depression of the respiratory or cardiovascular system, which can be especially dangerous for neonatal and juvenile and geriatric patients. A need therefore remains for improved methods for managing visceral pain during surgical procedures requiring general anesthesia and improved methods for MAC reduction.

The neurokinin-1 (NK-1) receptor is a receptor for the neurotransmitter substance P, and is distributed throughout the central nervous system. Certain neurokinin-1 (NK-1) receptor antagonists are known as having antidepressant, anxiolytic, and antiemetic properties. In particular, the NK-1 receptor antagonist aprepitant has provided a valuable tool for clinical management of the nausea and vomiting associated with cancer chemotherapy. The NK-1 receptor antagonist maropitant (available from Pfizer as Cerenia®), is an NK-1 receptor antagonist that is approved for use as an antiemetic in dogs.

SUMMARY OF THE INVENTION

In one aspect, the present disclosure provides a method of providing visceral analgesia in a mammalian subject in need thereof, the method comprising administering to the subject a therapeutically effective amount of a composition comprising a NK-1 receptor antagonist, a pharmaceutically acceptable salt thereof, a prodrug of the NK-1 receptor antagonist or pharmaceutically acceptable salt thereof, or a solvate or hydrate of the NK-1 compound, of the NK-1 receptor antagonist or of the pharmaceutically acceptable salt thereof.

In another aspect, the present disclosure provides a method for providing visceral analgesia to a mammalian subject in need thereof, the method comprising administering to the subject prior, during or after an administration of general anesthesia to the subject, a therapeutically effective amount of a composition comprising a NK-1 receptor antagonist, a pharmaceutically acceptable salt thereof, a prodrug of the NK-1 receptor antagonist or pharmaceutically acceptable salt thereof, or a solvate or hydrate of the NK-1 compound, of the NK-1 receptor antagonist or of the pharmaceutically acceptable salt thereof.

In the above methods, an exemplary NK-1 containing composition is a non-opioid composition.

In another aspect, the present disclosure provides a method of improving visceral analgesia in a mammalian subject in need thereof under general anesthesia, the method comprising: administering to the subject prior, during or after an administration of the general anesthesia, a therapeutically effective amount of a non-opioid composition comprising a NK-1 receptor antagonist, a pharmaceutically acceptable salt thereof, a prodrug of the NK-1 receptor antagonist or pharmaceutically acceptable salt thereof, or a solvate or hydrate of the NK-1 compound, of the NK-1 receptor antagonist or of the pharmaceutically acceptable salt thereof, wherein improving the visceral analgesia comprises, relative to a subject not administered the non-opioid composition, at least one of: reducing gastric regurgitation during surgery in the subject, stabilizing heart rate during surgery in the subject, stabilizing respiratory rate during surgery in the subject, and decreasing or eliminating clinical indications of post-operative discomfort in the subject.

In any of the above methods, the subject can be any mammal, including any non-human mammal such as but not limited to a canine or a feline. The NK-1 receptor antagonist is for example (7R,8S)—N-[(5-tert-Butyl-2-methoxyphenyl)methyl]-7-[di(phenyl)methyl]-1-azabicyclo[2.2.2]octan-8-amine (maropitant); (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant); or 5-([[(2R,3S)-2-((R)-1-[3,5-bis(trifluoromethyl)phenyl]ethoxy)-3-(4-fluorophenyl)morpholino]methyl)-1H-1,2,4-triazol-3(2H)-one (aprepitant). The composition can for example be administered parenterally or orally. For example, the composition may be subcutaneously administered, or intravenously administered. The amount of the NK-1 antagonist in the composition can be 0.1 mg/kg to 50 mg/kg of the subject's body weight, preferably 0.5 mg/kg to 10 mg/kg of the subject's body weight, and more preferably 1 mg/kg to 5 mg/kg of the subject's body weight. The method can be used for example for visceral pain relief in a ovariohysterectomy subject. In the method, the NK-1 receptor antagonist containing composition can be administered prior, during or after an administration of a general anesthesia such as inhalational anesthesia. The general anesthesia can be for example a halogenated ether such as but not limited to isoflurane, enflurane, halothane, sevoflurane, or desflurane.

DETAILED DESCRIPTION

Figure 1:
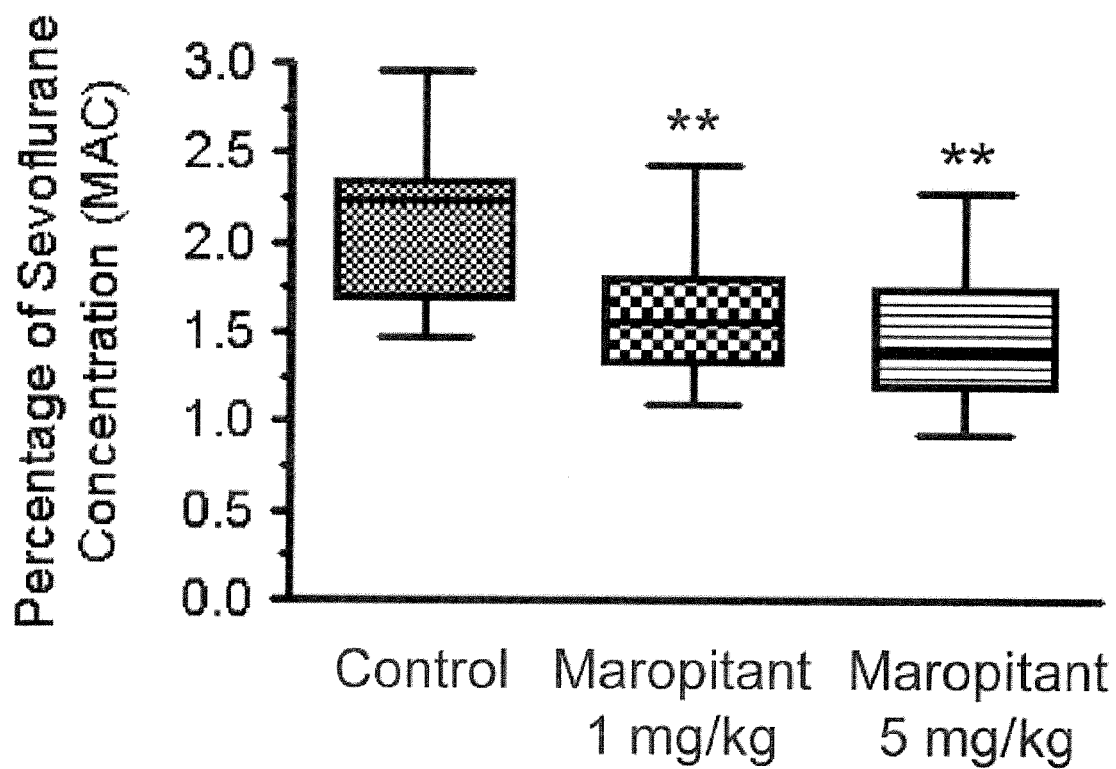
FIG. 1 is a bar graph showing sevoflurane MAC reduction by maropitant 1 mg/kg and 5 mg/kg in dogs during ovarian ligament stimulation.

The present disclosure is based in part on the discovery that administration of a composition comprising an NK-1 receptor antagonist such as maropitant to a mammalian subject before, during or after administration of a general anesthesia, provides visceral pain relief and reduces the anesthetic requirement during visceral stimulation, including during surgical procedures such as spay surgeries. The methods as described herein can be applied to any mammalian subject to provide visceral analgesia before, during or after administration of a general anesthesia to the subject. By reducing the amount of a general anesthetic such as an inhalational anesthetic required to attain the appropriate plane of anesthesia for the surgical procedure, the methods reduce anesthetic costs, improve the quality of anesthesia and decrease the potential for complications due to the anesthesia. Additionally, the methods are demonstrated to stabilize heart rate and breathing rate in subjects during painful visceral stimulation relative to the heart rate and breathing rate of subjects not administered any additional composition for analgesia, or subjects administered morphine for analgesia. Still further, the methods provide a more rapid and comfortable post procedure recovery, including but not limited to fewer overt signs of pain, reduced need for rescue analgesia, and more rapid return of appetite. Additionally, NK-receptor antagonists demonstrate few if any harmful side effects. By providing an alternative MAC reduction approach during painful visceral stimulation when anesthetics such as halogenated ethers are used, the methods allow clinicians to avoid the administrative and physical challenges associated with opioid use, including addiction and other harmful side effects including hallucinations and effects on the gastrointestinal, respiratory and cardiovascular systems. The methods also help avoid the development of chronic pain.

A. DEFINITIONS

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" refers to approximately a +/−10% variation from the stated value. It is to be understood that such a variation is always included in any given value provided herein, whether or not it is specifically referred to.

Unless defined otherwise herein, all technical and scientific terms used herein have the same meaning as commonly understood by one of ordinary skill in the art to which this invention belongs.

a) NK-1 Receptor

The term "NK-1 receptor" is used as commonly understood in the art to refer to the mammalian receptor also referred to as the tachykinin NK-1 receptor, which is a 407 amino acid protein having a molecular weight of 58.000, and is a member of family 1 (rhodopsin-like) of the G protein-coupled receptors, and conservative variants thereof.

b) NK-1 Receptor Antagonist

The term NK-1 receptor antagonist as used herein refers to a compound that selectively binds to the NK-1 receptor and reduces or eliminates the biological activity thereof, wherein selectively binding refers to about a 100-fold to 10.000-fold higher affinity of the antagonist to the NK-1 receptor relative to its affinity to either the NK-2 receptor or the NK-3 receptor. Such compounds include but are not limited to the compounds known as maropitant, casopitant, aprepitant, fosaprepitant, and vestipitant.

c) Non-Opioid

The term "non-opioid" as used herein refers to a composition that does not contain any agonist of the four mammalian opioid receptor subtypes (mu, kappa, delta and nociceptin). Opioid compounds include any naturally occurring opiates, semi-synthetic opioid derivates and synthetic opioid compounds, and thus a non-opioid composition includes none of these.

d) Pharmaceutically Acceptable Salt

The term "pharmaceutically acceptable salt" as used herein encompasses but is not limited to salts with inorganic acids and organic acids, such as for example hydrochlorate, phosphate, diphosphate, hydrobromate, sulfate, sulfinate, nitrate, malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH^2)_n-COOH$ where n is 0-4, and like salts.

e) Prodrug

As used herein, the term "prodrug" refers to a compound that is a precursor of another compound that is a pharmacologically active agent, wherein the precursor compound is administered to a subject in an inactive form and once administered is metabolized in vivo into the pharmacologically active agent.

f) Solvate and Hydrate

The term "solvate" as used herein refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules are water.

g) Subject

The term "subject" as used herein refers to a mammal, which may be a human or a non-human mammal such as but not limited to a dog, a cat, a non-human primate such as a monkey or ape, a rabbit, a rat, a mouse, or a pig.

h) Therapeutically Effective

The term "therapeutically effective amount" as used herein refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance may be ascertained by those skilled in the art or capable of determination by routine experimentation. As used herein the term encompasses an amount that is sufficient to prevent, reduce or eliminate clinical indicators of visceral pain in the subject.

B. METHODS

The present disclosure is based in part on the discovery that administration of a composition comprising an NK-1 receptor antagonist to a mammalian subject before, during or after administration of a general anesthesia, provides visceral pain relief and reduces the anesthetic requirements for visceral surgeries such as spay surgeries. For example, when a volatile anesthetic such as isoflurane is used for general anesthesia, the reduced minimum alveolar concentration (MAC) of isoflurane needed in the subject also administered the NK-1 receptor antagonist translates to a financial benefit of approximately 25-50 cents, per subject, per hour. Additionally, administration of the NK-1 receptor antagonist reduces or eliminates reliance on opioid substances for MAC reduction and post-operative analgesia. Post operative recovery is improved in visceral surgery subjects administered an NK-1 receptor antagonist before, during or after administration of a general anesthesia. For example, animals receiving an NK-1 receptor antagonist before spay surgeries exhibit a lower tendency to regurgitate or vomit during surgery as compared to animals that received morphine before surgery. Dogs receiving maropitant before spay surgeries exhibit fewer indicators of discomfort for a period of 2-3 hours following surgery, when compared to control dogs that did not receive the maropitant. The effect of NK-1 receptor antagonist administration on post operative comfort is comparable to that provided by morphine administration before spay surgery.

Additional benefits of avoiding the use of opioids for visceral pain management and MAC reduction during general anesthesia include certain post-operative benefits including reduced dysphoria, reduced nausea, fewer indicators of pain, and more rapid return of appetite. Additionally, unlike many opioids, NK-1 receptor antagonists such as maropitant do not impact gastrointestinal tract motility in dogs and other species. Morphine and other opioids decrease gastrointestinal motility and predispose to complications such as constipation in dogs and other species. Maropitant for example has not been reported to influence renal or urinary functions, while morphine and other opioids are well known to induce urinary retention in dogs and other species, which predisposes to damage of the urinary tract. In cesarean section surgeries in dogs, maropitant does not depress the respiratory or cardiovascular system and therefore offers neonatal pups a better chance of survival.

To provide visceral analgesia in a mammalian subject in need thereof as described herein, the subject is administered a therapeutically effective amount of a composition containing a NK-1 receptor antagonist, a pharmaceutically acceptable salt thereof, a prodrug of the NK-1 receptor antagonist or pharmaceutically acceptable salt thereof, or a solvate or hydrate of the NK-1 compound, of the NK-1 receptor antagonist or of the pharmaceutically acceptable salt thereof. The subject is for example a subject being prepared for, undergoing or recovering from a visceral surgery during which a general anesthesia is administered to achieve a surgical plane of anesthesia as determined by standards well known to human and veterinary clinicians and technicians. The method can be used for example for visceral pain relief in a subject undergoing a ovariohysterectomy (e.g. by laparotomy or laparoscopy) or caesarean section, or any surgery involving painful visceral stimulation.

The general anesthesia is for example a volatile anesthetic administered to the subject by inhalation, such as a halogenated ether including but not limited isoflurane, enflurane, halothane, sevoflurane, or desflurane. The NK-1 receptor antagonist can be administered to the subject before, during and/or after administration of general anesthesia. Preferably, the NK-1 receptor antagonist is administered before and/or during administration of the general anesthesia, to provide a MAC reduction effect during administration of the general anesthetic.

Specific NK-1 receptor antagonists for use in the presently disclosed methods, and pharmaceutical formulations containing them, include but are not limited to maropitant, casopitant, aprepitant, fosaprepitant and vestipitant and those generically and specifically disclosed in the following patent specifications which disclosures are incorporated herein by reference: U.S. Pat. Nos. 4,839,465; 5,576,317; 6,387,925; 5,719,147; 6,096,742; 5,691,336; EP 0327009; WO 91/12266; EP 0284942; GB 2216529; WO 91/02745; EP 0484719; WO 1/18016; EP 0482539; EP 0446706. A preferred NK-1 receptor antagonist is the compound (7R, 8S)—N-[(5-tert-Butyl-2-methoxyphenyl)methyl]-7-[di (phenyl)methyl]-1-azabicyclo[2.2.2]octan-8-amine (maropitant), described in U.S. Pat. No. 5,576,317.

It will be understood that a suitable dosage of the NK-1 receptor antagonist will depend on several factors including the subject, the NK-1 receptor antagonist selected, route of administration, and particular general anesthetic being used. A suitable dosage can be selected by the person of average skill in the art with reference to clinical indicators of visceral pain and discomfort that are generally evident during or after visceral stimulation and accompanying administration of the general anesthesia, and may be evident in the particular subject. For example, clinical indicators of visceral pain during visceral anesthesia and administration of the general anesthesia include elevated heart rate and/or elevated breathing rate relative to a clinically accepted average resting heart rate and breathing rate. Clinical indicators of visceral pain during initial recovery in the first 1-6 hours following return of consciousness may include for example indicators commonly accepted and used by human and veterinary clinicians and health care professionals to assess pain status, including those based on self-report, observational (behavioral), or physiological data. General indicators of pain or comfort level include for example a general return to normal bodily functions and mobility, return of appetite, general responsiveness, and apparent readiness for hospital discharge. Indicators may be used that are associated or graded with reference to a known clinical pain scale, such as but not limited to the Visual Analogue Pain Scale (or Score), Alder Hey Triage Pain Score, Brief Pain Inventory (BPI), Dallas Pain Questionnaire, Dolorimeter Pain Index (DPI), Faces Pain Scale-Revised (FPS-R), Face Legs Activity Cry Consolability scale, Lequesne: pain and disability, McGill Pain Questionnaire (MPQ), Descriptor differential scale (DDS), Neck Pain and Disability Scale—NPAD, Numerical 11 point box (BS-11), Numeric Rating Scale (NRS-11), Roland-Morris Back Pain Questionnaire, or the Wong-Baker FACES Pain Rating Scale.

Although the amount of the NK-1 antagonist in the composition may vary according to factors such as those listed above, a suitable dosage range is for example 0.1 mg/kg to 50 mg/kg of the subject's body weight, preferably 0.5 mg/kg to 10 mg/kg of the subject's body weight, and more preferably 1 mg/kg to 5 mg/kg of the subject's body weight. These ranges are exemplary amounts that provide for example a therapeutically effective amount of the NK-1 receptor antagonist for example in dogs and cats as described herein.

For administration, the NK-1 receptor antagonist can be incorporated into a pharmaceutical composition suitable for administration to a subject. Such a pharmaceutical composition comprises at least one NK-1 receptor antagonist such as maropitant and a pharmaceutically acceptable carrier, excipient or diluent. Preferred pharmaceutical compositions comprise a therapeutically effective amount of one or more NK-1 receptor antagonists, together with a pharmaceutically acceptable diluent, carrier, solubilizer, emulsifier, preservative and/or adjuvant. Pharmaceutically preferred formulation materials are preferably nontoxic to recipients at the dosages and concentrations employed. The pharmaceutical composition may contain one or more various formulation materials for modifying, maintaining or preserving the composition or properties of the composition, for example, the color, consistency, isotonicity, odor, osmolarity, pH, sterility, stability, viscosity and other properties. Such formulation materials are generally well known, are described for example in REMINGTON'S PHARMACEUTICAL SCIENCES, 18$^{th}$ Ed. (A. R. Gennaro, ed.) 1990, Mack Publishing Company. Non-limiting examples of suitable formulation materials include amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Optimal pharmaceutical formulations can be readily determined by one skilled in the art depending upon, for example, the intended route of administration, delivery format and desired dosage.

The pharmaceutical composition may comprise at least one additional therapeutic agent for controlling, i.e. reducing visceral pain in the subject. The additional agent can be for example a therapeutic agent, a muscle relaxant, narcotic, a steroid, a non-steroid anti-inflammatory drug (NSAID), analgesic, anesthetic, sedative, local anesthetic, or neuromuscular blocker. Preferably the composition is a non-opioid composition. In certain instances, however, use of NSAIDS may preferably be avoided to avoid the potentially harmful side effects associated with use of NSAIDS, including renal failure, GI ulcers and even death.

The NK-1 receptor antagonist composition can be administered to the subject by any of a variety of methods known in the art, although for many therapeutic applications, the route/mode of administration is subcutaneous injection, intravenous injection or infusion. Administration can be systemic or local. As will be appreciated by the skilled artisan, the route and/or mode of administration will vary depending upon the desired results. For example, pharmaceutical compositions containing the NK-1 receptor antagonist may be formulated for administration to a subject by parenteral, intradermal, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, oral, bolus, vaginal, rectal, buccal, sublingual, intranasal, or transdermal.

The NK-1 receptor antagonist composition may be prepared with a carrier that will protect the compound against rapid release, such as a controlled release formulation, including polymers, implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art, and are described for example in *Sustained and Controlled Release Drug Delivery Systems*, J. R. Robinson, ed., Marcel Dekker, Inc., New York, 1978.

By providing for MAC reduction and visceral pain relief without the need to resort to opioids such as morphine, the methods also improve visceral analgesia in a mammalian subject under general anesthesia, by providing any one or more of the following effects in the subject: reducing gastric regurgitation during surgery in the subject, stabilizing heart rate during surgery in the subject, stabilizing respiratory rate during surgery in the subject, and decreasing or eliminating clinical indications of post-operative discomfort in the subject. It will be understood that these effects can be readily determined or measured using readily observable clinical indicators and procedures known to those of skill in the art and are determined in comparison to a subject not administered the non-opioid, NK-1 receptor antagonist composition.

C. ADAPTATIONS OF THE METHODS OF THE PRESENT DISCLOSURE

By way of example, not of limitation, examples of the present invention shall now be given.

EXAMPLE 1

Maropitant Decreases the Sevoflurane MAC During Visceral Stimulation in Dogs

The NK1 receptor antagonist maropitant, available as Cerenia® from Pfizer, is an antiemetic approved for use in dogs. The ability of maropitant to impact the sevoflurane minimum alveolar concentration (MAC) level needed for surgery was tested in canine subjects. The eight animals were 1 year old, intact female, Walker hound mix. A first group was administered 1 mg/kg maropitant, I.V. over 5 minutes then 30 µg/kg/h. A second group was administered 5 mg/kg maropitant, I.V. over 5 minutes then 150 µg/kg/h. General anesthesia was induced using sevoflurane as described below and otherwise according to standard veterinary procedure. Animals were maintained in dorsal recumbency. MAC reduction effect was tested by stimulation of the ovarian ligament. Ovariectomy was performed on each animal at the end of the study.

In each animal, sterile laparoscopy was performed to access the right ovary. Following thirty minutes of sevoflurane at steady state, end-tidal sevoflurane concentration was measured with a calibrated agent analyzer (Biochem). End-tidal O2 was >90% and CO2 30-40%. Esophageal temperature was 37.5-39° C. Ovarian ligament stimulation was performed using 6.61 Newton's of force with a calibrated grass force displacement transducer. FIG. 1 is a bar graph comparing the MAC reduction using I.V. maropitant during isoflurane anesthesia. The observed MAC reduction is reported at sea level (mean±SD), and compared to published results for other MAC reduction agents in Table 1.

TABLE 1

Comparative MAC Reduction by Alternative MAC reduction Agents

| MAC reduction agent, dose | Anesthetic agent | MAC Reduction (%, mean ± SD) |
|---|---|---|
| Maropitant 1 mg/kg | sevoflurane | 24 |
| Maropitant 5 mg/kg | sevoflurane | 30 |
| Morphine 1 mg/kg | halothane and isoflurane | 35, 39 (Steffey et al., 1993) |
| Fentanyl 10 µg/kg; 0.3 µg/kg/min | isoflurane | 53 (Hellyer et al., 2001) |
| Butorphanol 0.1-4 mg/kg | enflurane | 8 (Murphy and Hug, 1982) |
| Ketamine ~1-2 mg/kg | sevoflurane | 47 (calculated from Pypendop et al., 2007) |
| Lidocaine 2 mg/kg; 50 & 200 µg/kg/min | isoflurane | 19, 43 (Valverde et al., 2004) |
| Dexmedetomidine 0.5 & 3 µg/kg; 0.5 & 3 µg/kg/h | isoflurane | 18, 59 (Pascoe et al., 2006) |
| MLK 3.3 + 50 + 10 µg/kg/min | isoflurane | 45 (Muir et al., 2003) |
| Acepromazine 0.04 mg/kg | halothane | 40 (Heard et al., 1986) |
| Carprofen 4 mg/kg | sevoflurane | 12 (Yamashita et al., 2008) |
| Meloxciam 0.2 mg/kg | sevoflurane | 23 (Yamashita et al., 2008) |

Maropitant administered prior to surgery at 1 mg/kg reduced the anesthetic requirements by 24%, and when administered at 5 mg/kg reduced the anesthetic requirements by 30%. These results indicated for the first time that maropitant decreases the anesthetic requirements during stimulation of the ovarian ligament in dogs, and thus provide the first demonstration of the use of NK1 receptor antagonist to manage visceral pain in dogs.

EXAMPLE 2

Maropitant Induced Analgesia and Comfort in Dogs During and After Spay Surgery

Having shown as described in Example 1 that maropitant has visceral analgesic and anesthetic sparing properties in dogs, including the effect of increasing the pain threshold during anesthesia by 24-30%, a follow up clinical trial was conducted to test the analgesic effect of maropitant in dogs during spay surgery (laparotomy ovariohysterectomy). The maropitant analgesic effect was directly compared with the analgesic effect elicited by morphine, a standard common analgesic used in human and veterinary medicine.

Figure 2:
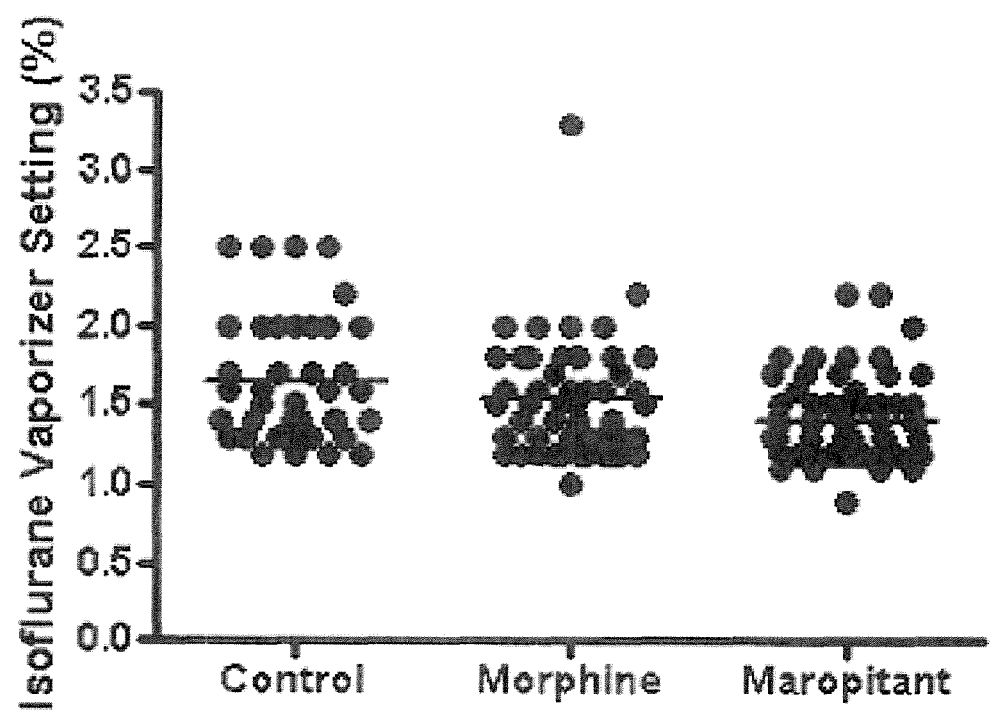
FIG. 2 is a scatter plot of isoflurane requirements (isoflurane vaporizer setting, %) during ovarian ligament stimulation in forty female dogs divided among a control group, a group administered 0.5 mg/kg subcutaneous morphine for analgesia and a group administered 1 mg/kg maropitant the NK-1 receptor antagonist maropitant, subcutaneous, before administration of isoflurane.

Forty (40) female dogs were admitted in the clinical trial and divided into three groups for comparison: a control, a maropitant and a morphine group. Dogs in the control group received 0.1 ml/kg SQ of sterile physiologic saline before anesthesia. Dogs in the morphine group received 0.5 mg/kg of morphine SQ before anesthesia for pain management. Dogs in the maropitant group received 1 mg/kg SQ of maropitant before anesthesia for pain management. The results are shown in FIGS. 2-6. As shown in FIG. 2, the maropitant group required less isoflurane anesthesia during ovary ligation and resection during surgery when compared to the control group (1.41±0.25% vs 1.65±0.39%; p<0.01), which indicates visceral analgesia and anesthesia sparing in the maropitant group. No difference was observed when comparing the maropitant group with the morphine group during visceral stimulation (1.53±0.37%).

Figure 4:
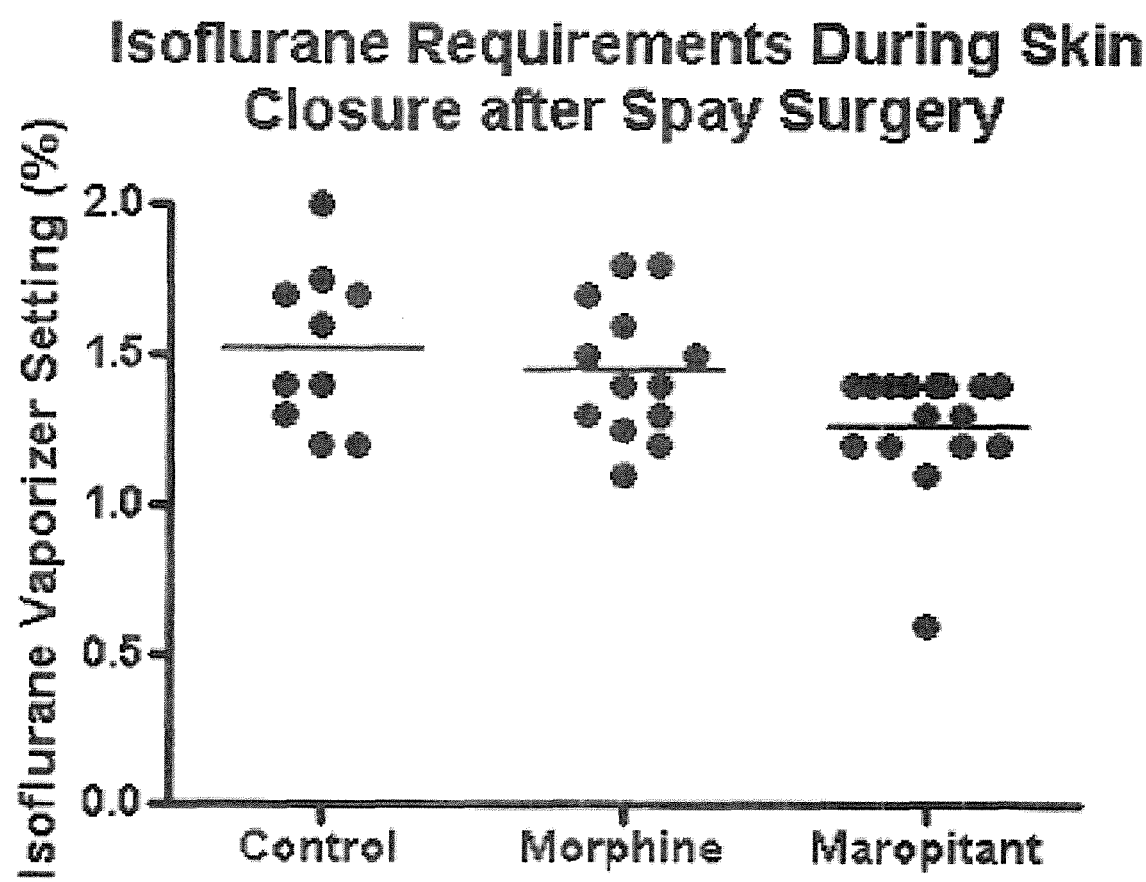
FIG. 4 is a scatter plot of isoflurane requirements (isoflurane vaporizer setting, %)) during skin closure following spay surgery in dogs in the control group, the morphine group and the maropitant group.

Similarly, as shown in FIG. 4, the maropitant group required less isoflurane anesthesia during skin closure when compared to control at the end of surgery (1.26±0.19% vs 1.52±0.26%; p<0.05), which indicates visceral-somatic analgesia and anesthesia sparing in the maropitant group. The morphine group required 1.45±0.22% isoflurane during skin closure, which was not different when compared to the maropitant or control groups.

Figure 3:
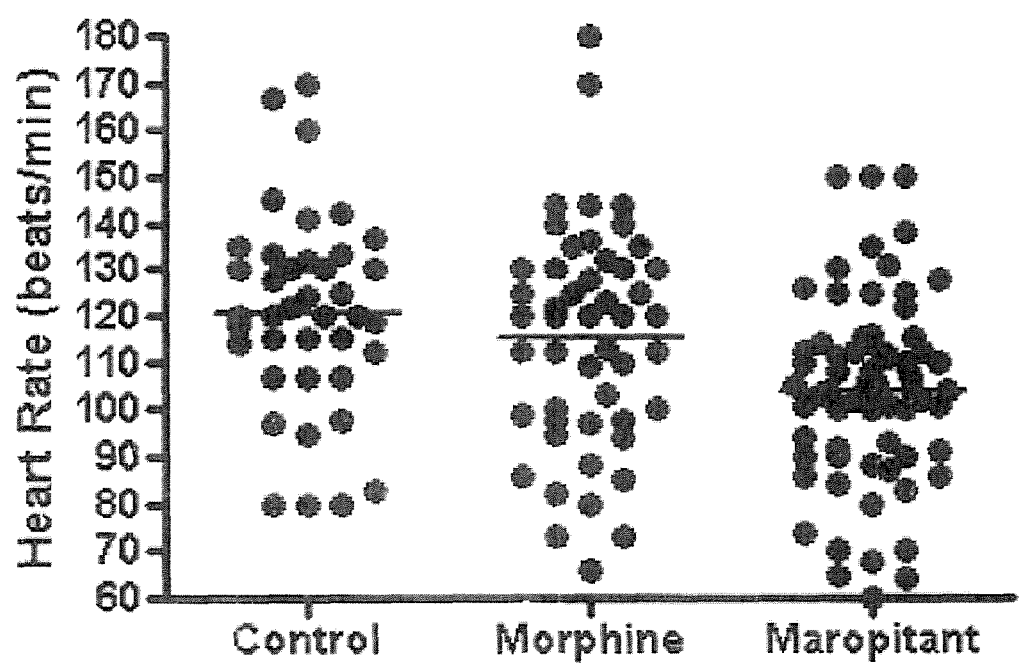
FIG. 3 is a scatter plot of heart rate (beats/min) during the ovarian ligament stimulation in dogs in the control group, the morphine group and the maropitant group.
Figure 5:
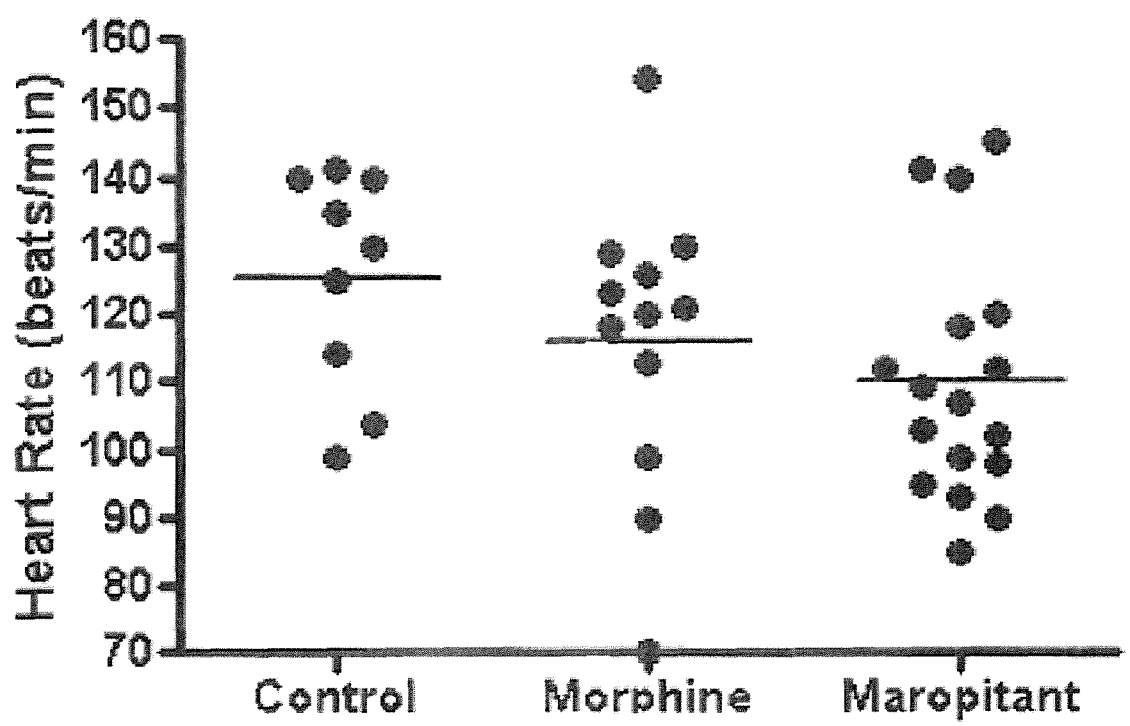
FIG. 5 is a scatter plot of heart rate (beats/min) during skin closure following spay surgery in dogs in the control group, the morphine group and the maropitant group.

Of clinical interest, as shown in FIGS. 3 and 5, the dogs in the maropitant group maintained a lower and more stable heart rate throughout surgery, indicating a more stable plain of anesthesia independent of the surgical pain stimulation. The maropitant group maintained an average heart rate of 103±20 beats per minute, while the control and morphine groups maintained an average heart rate of 120±21, and 115±23 beats per minute, respectively. The dogs in the maropitant group maintained more stable respiratory activity. The maropitant group respiratory rate throughout surgery was an average of 21±12 breaths per minute, and only 35% of the subjects responded with panting during surgical painful stimulation. Dogs in the control group maintained an average respiratory rate throughout surgery of 23±12 breaths per minute, no different than the maropitant group, however 67% of the dogs responded to surgical stimulation with panting. The morphine group maintained an average respiratory rate of 27±20 breaths per minute, and 38% of the dogs responded to surgical stimulation, comparable to the results observed in the maropitant group. As a potential complication during surgery, dogs in the morphine group had the highest incidence of gastric regurgitation into the esophagus. In 29% of the dogs in the morphine group, the esophageal pH decreased below 5 during surgery. By comparison, only 12% of the dogs in the maropitant group, and 10% of the dogs in the control group decreased their esophageal pH below 5 throughout surgery. Gastric reflux during surgery predisposes to esophagitis and potentially esophageal stricture or aspirational pneumonia.

Figure 6:
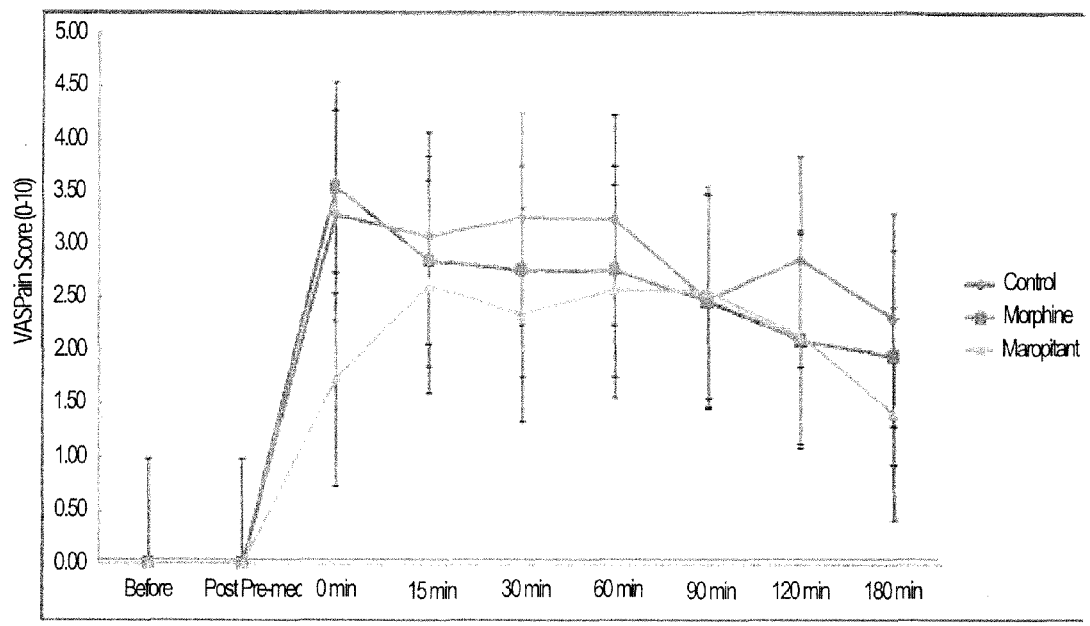
FIG. 6 is a graph of pain assessment over time in the dogs in the control group, the morphine group and the maropitant group, using the Visual Analogue Pain Scale score.

Following surgery and return to consciousness from anesthesia, the dogs in the morphine group generally fared worse when compared to the maropitant group. As shown in FIG. 6, during pain assessment using the Visual Analogue Pain Scale (0-10) conducted during the three hours following recovery from anesthesia, the dogs in the maropitant group showed fewer overt signs of pain and discomfort, and generally appeared more comfortable as compared to the control group. During the same period, the same was observed for the morphine group relative to control, but only through the initial two hours of assessment. Overall, a higher percentage of dogs in the morphine group appeared nauseous, dysphoric and/or uncomfortable during the recovery period as compared to the maropitant group.

Table 2 sets forth the average number of morphine and carprofen rescue analgesia doses required during the recovery period, for each group.

TABLE 2

Average number of morphine and carprofen rescue analgesia doses required per group during recovery

|  | Control | Morphine | Maropitant |
| --- | --- | --- | --- |
| Post-Operative Morphine Rescue Analgesia (0.1 mg/kg, IV) | 2.5 | 2 | 1.8 |

TABLE 2-continued

Average number of morphine and carprofen rescue analgesia doses required per group during recovery

|  | Control | Morphine | Maropitant |
| --- | --- | --- | --- |
| Post-Operative Carprofen Rescue Analgesia (4 mg/kg, IV) | 30% | 30% | 18% |

Thus, dogs in the maropitant group on average needed lower doses of morphine for post-operative rescue analgesia, and needed it less frequently. Dogs in the maropitant group on average required a lower morphine dose for post-operative rescue analgesia, as compared to both the control and the morphine group. Additionally, only 18% of the dogs in the maropitant group required a carprofen analgesia rescue dose to achieve comfort during the post-operative period, while 30% of the dogs in the morphine group, and 30% of the dogs in the control group required a carprofen analgesia rescue dose to achieve comfort during the post-operative period.

Dogs in the maropitant group ate also more promptly following anesthesia/surgery and appeared less nauseous overall, which supported earlier hospital discharge because of the resulting more rapid return to normal bodily function. 65% of the dogs in the maropitant group started eating within 3 hours following surgery, and only 29% showed overt signs of nausea (e.g., excessive salivation, drowsy appearance). In comparison, only 1% of the dogs in the control group ate within 3 hours after surgery, and 60% of the dogs showed overt signs of nausea. Of the morphine group, 26% ate within 3 hours following surgery, and 31% showed overt signs of nausea.

This clinical trial confirmed the findings observed in the study described in Example 1 which first addressed visceral pain management using maropitant in dogs. Maropitant provides appropriate analgesia for spay surgeries in dogs, which analgesic affect appears to be comparable or even better compared to 0.5 mg/kg of morphine. In addition, the incidence and degree of collateral effects observed during and post surgery in the maropitant group were reduced relative to those observed in the morphine group (e.g., nausea, dysphoria and gastric reflux). This is the first clinical trial showing that maropitant has sufficient analgesic properties for managing visceral pain in spay surgeries in dogs, and reduces the incidence and severity of the collateral effects relative to those observed with morphine when used as a MAC reduction agent.

EXAMPLE 3

Maropitant Decreases the Sevoflurane Mac During Visceral Stimulation in Cats

Maropitant is the first candidate analgesic with antiemetic properties for cats. No adverse effects such as constipation, diarrhea, gastric ulcers, liver toxicity or renal failure have been reported while using maropitant in cats at the recommended clinical doses, while such complications have been described when other analgesics are used in cats. Accordingly, the use of maropitant to promote analgesia in cats during ovarian ligament stimulation was also investigated. Following the results obtained in dogs as described in the previous examples, anesthetic requirements were expected to decrease in cats when maropitant is administered, if maropitant has comparable analgesic properties in cats.

Figure 7:
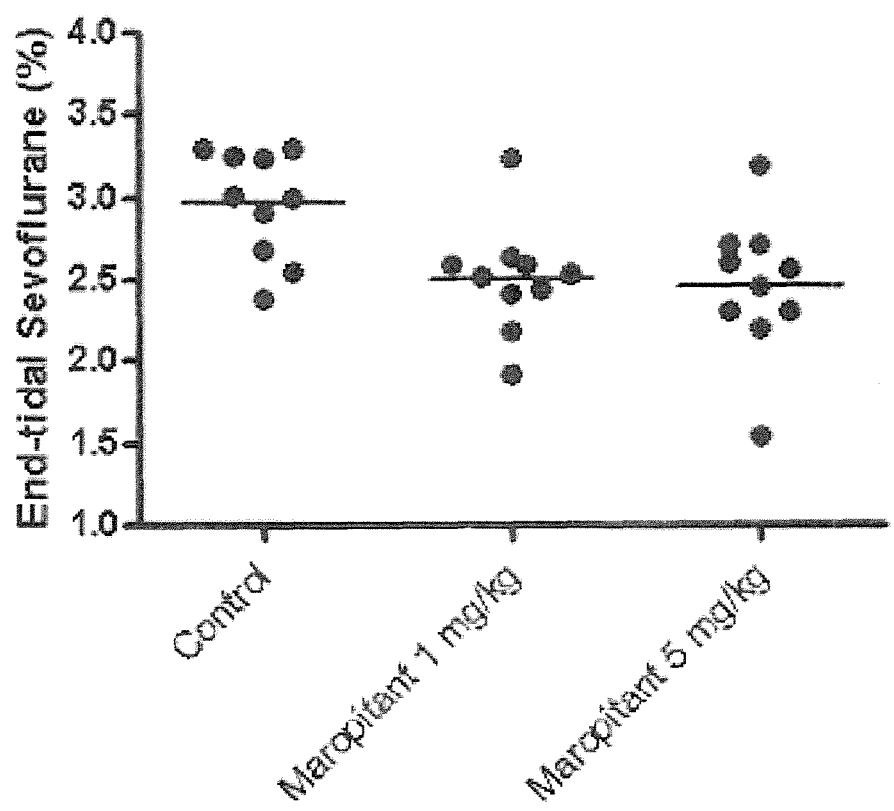
FIG. 7 is a scatter plot of sevoflurane requirements (end-tidal sevoflurane, %) during ovary and ovarian ligament stimulation in ten female cats divided among a control group, a group administered 1.0 mg/kg I.V. maropitant for analgesia and a group administered 5.0 mg/kg I.V. maropitant during visceral stimulation under sevoflurane anesthesia.

Ten (10) female cats were anesthetized with sevoflurane. Following stabilization, the right ovarian ligament was accessed using a laparoscopic approach to determine the anesthetic minimum alveolar concentration (MAC). The ovarian ligament was stimulated using 500 grams of traction force. The results are shown in FIG. 7. The MAC is reported as mean±SD, adjusted for calibration values and to sea-level. The anesthetic requirement MAC during stimulation of the ovary was 2.96±0.32%. Administration of maropitant 1 mg/kg IV decreased the anesthetic requirements MAC to 2.50±0.33% (15%, p<0.01). A higher maropitant dose of mg/kg IV did not change the anesthetic requirement MAC further (2.45±0.43%; 17%).

The results indicate that maropitant decreases the anesthetic requirements during visceral stimulation of the ovarian ligament in cats, an indication that maropitant provides visceral pain relief and analgesia in cats. While the anesthetic sparing effect observed in cats was not in this case as potent as the results observed in dogs, these results provide the first description of maropitant administration to manage visceral pain in cats.

One skilled in the art would readily appreciate that the methods described in the present disclosure are well adapted to carry out the objects and obtain the ends and advantages mentioned, as well as those inherent therein. The methods, procedures, treatments, described herein are merely representative and exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

REFERENCES

Steffey, E. P.; Eisele, J. H.; Baggot, J. D.; Woliner, M. J.; Jarvis, K. A.; Elliott, A. R., Influence of inhaled anesthetics on the pharmacokinetics and pharmacodynamics of morphine, Anesth Analg 77(2): 346-51, 1993

Hellyer P W, Mama K R, Shafford H L, Wagner A E, Kollias-Baker C., Effects of diazepam and flumazenil on minimum alveolar concentrations for dogs anesthetized with isoflurane or a combination of isoflurane and fentanyl, Am J Vet Res. 2001, Apr; 62(4):555-60.

Murphy M R, Hug C C Jr., The enflurane sparing effect of morphine, butorphanol, and nalbuphine, Anesthesiology, 1982 Dec; 57(6):489-92.

Pypendop B H, Solano A, Boscan P, Ilkiw J E., Characteristics of the relationship between plasma ketamine concentration and its effect on the minimum alveolar concentration of isoflurane in dogs, Vet Anaesth Analg. 2007 May; 34(3):209-12.

Valverde A, Doherty T J, Hernandez J, Davies W., Effect of lidocaine on the minimum alveolar concentration of isoflurane in dogs, Vet Anaesth Analg. 2004 Oct; 31(4):264-71.

Pascoe P J, Raekallio M, Kuusela E, McKusick B, Granholm M., Changes in the minimum alveolar concentration of isoflurane and some cardiopulmonary measurements during three continuous infusion rates of dexmedetomidine in dogs, Vet Anaesth Analg. 2006 Mar; 33(2):97-103.

Muir W W, Effects of morphine, lidocaine, ketamine, and morphine-lidocaine-ketamine drug combination on minimum alveolar concentration in dogs anesthetized with isoflurane, 3rd, Wiese A J, March P A., Am J Vet Res. 2003 Sep; 64(9):1155-60, Am J Vet Res. 1986 Oct; 47(10):2113-5.

Heard D J, Webb A I, Daniels R T, Effect of acepromazine on the anesthetic requirement of halothane in the dog, Yamashita K, Okano Y, Yamashita M, Umar M A, Kushiro T, Muir W W., Effects of carprofen and meloxicam with or without butorphanol on the minimum alveolar concentration of sevoflurane in dogs, J Vet Med. Sci. 2008 Jan; 70(1):29-35.

What is claimed is:

1. A method of improving visceral analgesia during a visceral surgery in an anesthetized canine subject in need thereof, the method comprising:
   administering to the subject an amount of an inhalational general anesthetic selected from the group consisting of isoflurane, enflurane, halothane, sevoflurane, or desflurane;
   parenterally or orally administering to the subject 0.1 mg/kg to 50 mg/kg of the subject's body weight of a composition comprising (7R,8S)-N-[(5-tert-Butyl-2-methoxyphenyl)methyl]-7-[di(phenyl)methyl]-1-azabicyclo[2.2.2]octan-8-amine or a pharmaceutically acceptable salt thereof, before or during administration of the inhalational general anesthetic to the subject;
   and conducting the visceral surgery, wherein administering the inhalational general anesthetic comprises administering a reduced amount of the general anesthetic relative to a subject not administered the NK-1 receptor antagonist composition, the reduced amount determined by a reduction of at least about 24% in the minimum alveolar concentration (MAC) of the inhalational anesthetic sufficient for the subject to achieve a surgical plane of anesthesia.

2. The method of claim 1, wherein the composition is subcutaneously administered.

3. The method of claim 1, wherein the composition is intravenously administered.

4. The method of claim 1, wherein the amount of the NK-1 antagonist is 0.5 mg/kg to 10 mg/kg of the subject's body weight.

5. The method of claim 1, wherein the amount of the NK-1 antagonist is 1 mg/kg to 5 mg/kg of the subject's body weight.

6. The method of claim 1, wherein the subject in need of visceral analgesia is a ovariohysterectomy subject.

7. A method of reducing the amount of general anesthetic required during a visceral surgery in a canine subject in need thereof, the method comprising:
   administering to the subject an amount of a general anesthetic selected from the group consisting of isoflurane, enflurane, halothane, sevoflurane, or desflurane; and
   parenterally or orally administering to the subject prior or during the administration of the general anesthetic 0.1 mg/kg to 50 mg/kg of the subject's body weight of (7R,8S)-N-[(5-tert-Butyl-2-methoxyphenyl)methyl]-7-[di(phenyl)methyl]-1-azabicyclo[2.2.2]octan-8-amine or a pharmaceutically acceptable salt thereof,
   wherein the amount of general anesthetic required during the visceral surgery for the subject to achieve a surgical plane of anesthesia is reduced for the subject relative to a subject not administered the non-opioid composition, the reduced amount determined by a reduction of at least about 24% in the minimum alveolar concentration (MAC) of the inhalational anesthetic.

8. The method of claim 7, wherein reducing the amount of general anesthetic required during the visceral surgery produces in the subject, relative to a subject not administered the non-opioid composition, at least one of: reduced gastric regurgitation during the surgery, increased heart rate stability during the surgery, and increased respiratory rate stability during the surgery.

9. The method of claim 7, wherein the composition is subcutaneously administered.

10. The method of claim 7, wherein the composition is intravenously administered.

11. The method of claim 7, wherein the amount of the NK-1antagonist is 0.5 mg/kg to 10 mg/kg of the subject's body weight.

12. The method of claim 7, wherein the amount of the NK-1antagonist is 1 mg/kg to 5 mg/kg of the subject's body weight.

13. The method of claim 7, wherein the subject is a ovariohysterectomy subject.

14. The method of claim 7, wherein the minimum alveolar concentration of the inhalation anesthesia is reduced by about 25% to about 30%.

15. The method of claim 1, wherein reducing the amount of general anesthetic required during the visceral surgery produces in the subject, relative to a subject not administered the non-opioid composition, at least one of: reduced gastric regurgitation during the surgery, increased heart rate stability during the surgery, and increased respiratory rate stability during the surgery.

* * * * *